(12) United States Patent
Dos Santos et al.

(10) Patent No.: US 8,986,240 B2
(45) Date of Patent: Mar. 24, 2015

(54) CORRUGATED MEMBRANE ACTUATORS

(75) Inventors: Cesario P Dos Santos, Aliso Viejo, CA (US); Robert J Sanchez, Jr., Oceanside, CA (US); Leslie A Field, Portola Valley, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 565 days.

(21) Appl. No.: 13/396,011

(22) Filed: Feb. 14, 2012

(65) Prior Publication Data

US 2013/0211313 A1    Aug. 15, 2013

(51) Int. Cl.
*A61F 9/00* (2006.01)
*A61M 5/142* (2006.01)
*A61F 9/007* (2006.01)
*A61M 39/24* (2006.01)

(52) U.S. Cl.
CPC .... *A61F 9/00781* (2013.01); *A61M 2039/2433* (2013.01)
USPC .............................................. 604/9

(58) Field of Classification Search
CPC ........... A61M 1/00; A61M 5/00; A61M 5/14; A61M 5/142; A61M 27/00; A61M 31/00; A61B 5/00; A61F 2/04; A61F 9/00; A61F 9/007; A61H 32/00; A61H 35/00; A61K 9/00
USPC .......... 604/8–10, 294, 890.1–892.1; 606/4–6
See application file for complete search history.

(56) References Cited

U.S. PATENT DOCUMENTS

| 4,089,329 A | 5/1978 | Couvillon et al. |
| 4,206,762 A | 6/1980 | Cosman |
| 4,457,757 A | 7/1984 | Molteno |

(Continued)

FOREIGN PATENT DOCUMENTS

| DE | 4438201 | 5/1996 |
| EP | 2427097 | 3/2012 |

(Continued)

OTHER PUBLICATIONS

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

(Continued)

*Primary Examiner* — Melanie Hand
(74) *Attorney, Agent, or Firm* — Haynes and Boone, LLP

(57) ABSTRACT

An IOP control valve is disclosed. The IOP control valve comprises a corrugated membrane and a housing including a fluid inlet and a fluid outlet. The corrugated membrane is anchored within the housing to form a reference chamber on a first side of the corrugated membrane and a fluid flow channel on a second opposing side of the membrane. The reference chamber has a reference chamber pressure representative of atmospheric pressure. The fluid flow channel can selectively increase and decrease in size to permit fluid to flow from the fluid inlet to the fluid outlet. The corrugated membrane is configured to affect flow through the fluid flow channel from the fluid inlet to the fluid outlet by deflecting in response to pressure differentials of the reference chamber pressure and the fluid flow channel pressure acting on the opposing sides of the corrugated membrane.

35 Claims, 10 Drawing Sheets

(56) References Cited

U.S. PATENT DOCUMENTS

| | | | |
|---|---|---|---|
| 4,656,827 A | 4/1987 | Puillet | |
| 4,750,901 A | 6/1988 | Molteno | |
| 4,922,913 A | 5/1990 | Waters et al. | |
| 5,005,577 A | 4/1991 | Frenkel | |
| 5,178,604 A | 1/1993 | Baerveldt | |
| 5,179,953 A | 1/1993 | Kursar | |
| 5,397,300 A | 3/1995 | Baerveldt | |
| 5,476,445 A | 12/1995 | Baerveldt | |
| 5,558,629 A | 9/1996 | Baerveldt | |
| 5,573,646 A | 11/1996 | Saito et al. | |
| 5,626,558 A | 5/1997 | Suson | |
| 5,681,275 A | 10/1997 | Ahmed | |
| 5,910,110 A | 6/1999 | Bastable | |
| 6,007,511 A | 12/1999 | Prywes | |
| 6,048,328 A | 4/2000 | Haller et al. | |
| 6,090,062 A | 7/2000 | Sood et al. | |
| 6,447,449 B1 | 9/2002 | Fleischman et al. | |
| 6,468,283 B1 | 10/2002 | Richter et al. | |
| 6,544,208 B2 | 4/2003 | Ethier et al. | |
| 6,579,235 B1 | 6/2003 | Abita et al. | |
| 6,589,198 B1 | 7/2003 | Soltanpour et al. | |
| 6,682,500 B2 | 1/2004 | Soltanpour et al. | |
| 6,712,764 B2 | 3/2004 | Jeffries et al. | |
| 6,749,568 B2 | 6/2004 | Fleischman et al. | |
| 6,939,299 B1 | 9/2005 | Petersen et al. | |
| 7,137,952 B2 | 11/2006 | Leonardi et al. | |
| 7,169,106 B2 | 1/2007 | Fleischman et al. | |
| 7,252,006 B2 | 8/2007 | Tai et al. | |
| 7,354,416 B2 | 4/2008 | Quiroz-Mercado et al. | |
| 7,409,863 B2 | 8/2008 | Bateman et al. | |
| 7,612,328 B2 | 11/2009 | Kaiser | |
| 7,824,699 B2 | 11/2010 | Ralph et al. | |
| 7,882,612 B2 | 2/2011 | Dehe et al. | |
| 8,182,435 B2 | 5/2012 | Dacquay et al. | |
| 8,257,295 B2 | 9/2012 | Rickard et al. | |
| 2001/0000527 A1 | 4/2001 | Yaron et al. | |
| 2002/0019607 A1 | 2/2002 | Bui | |
| 2002/0049374 A1 | 4/2002 | Abrea | |
| 2002/0087111 A1 | 7/2002 | Ethier et al. | |
| 2002/0099359 A1 | 7/2002 | Santini, Jr. et al. | |
| 2002/0143284 A1 | 10/2002 | Tu et al. | |
| 2002/0193674 A1 | 12/2002 | Fleischman et al. | |
| 2003/0078487 A1 | 4/2003 | Jeffries et al. | |
| 2003/0225318 A1 | 12/2003 | Montegrande et al. | |
| 2004/0013702 A1 | 1/2004 | Glover | |
| 2004/0059248 A1 | 3/2004 | Messner et al. | |
| 2004/0073137 A1 | 4/2004 | Lloyd et al. | |
| 2004/0111050 A1 | 6/2004 | Smedley et al. | |
| 2004/0116794 A1 | 6/2004 | Fink et al. | |
| 2004/0186367 A1 | 9/2004 | Fresco | |
| 2004/0254438 A1 | 12/2004 | Chuck et al. | |
| 2004/0254517 A1 | 12/2004 | Quiroz-Mercado et al. | |
| 2004/0254521 A1 | 12/2004 | Simon | |
| 2005/0049578 A1 | 3/2005 | Tu et al. | |
| 2005/0159660 A1 | 7/2005 | Montegrande et al. | |
| 2005/0271704 A1 | 12/2005 | Tu et al. | |
| 2005/0273033 A1 | 12/2005 | Grahn et al. | |
| 2006/0131350 A1 | 6/2006 | Schechter et al. | |
| 2007/0019156 A1 | 1/2007 | Fink | |
| 2007/0032757 A1 | 2/2007 | Medow et al. | |
| 2007/0106199 A1 | 5/2007 | Krivoy et al. | |
| 2007/0109117 A1 | 5/2007 | Heitzmann et al. | |
| 2007/0123767 A1 | 5/2007 | Montegrande et al. | |
| 2007/0129623 A1 | 6/2007 | Fleischman et al. | |
| 2007/0212397 A1 | 9/2007 | Roth | |
| 2008/0015421 A1 | 1/2008 | Penner | |
| 2008/0077127 A1 | 3/2008 | Gao et al. | |
| 2008/0125691 A1 | 5/2008 | Yaron et al. | |
| 2008/0129486 A1 | 6/2008 | Jeckelmann et al. | |
| 2008/0215062 A1 | 9/2008 | Bowen et al. | |
| 2008/0228127 A1 | 9/2008 | Burns et al. | |
| 2009/0036819 A1 | 2/2009 | Tu et al. | |
| 2009/0069648 A1 | 3/2009 | Irazqui et al. | |
| 2009/0076367 A1 | 3/2009 | Sit et al. | |
| 2009/0143713 A1 | 6/2009 | Van Dam et al. | |
| 2009/0227933 A1 | 9/2009 | Karageozian | |
| 2009/0275924 A1 | 11/2009 | Lattanzio et al. | |
| 2009/0312742 A1 | 12/2009 | Pang et al. | |
| 2010/0010416 A1 | 1/2010 | Juan, Jr. et al. | |
| 2010/0042209 A1 | 2/2010 | Guarnieri | |
| 2010/0121348 A1 | 5/2010 | Van Der Burg et al. | |
| 2010/0222769 A1* | 9/2010 | Meng et al. | 604/891.1 |
| 2010/0234717 A1 | 9/2010 | Wismer | |
| 2010/0253167 A1 | 10/2010 | Charnley et al. | |
| 2011/0046536 A1 | 2/2011 | Stegmann et al. | |
| 2011/0071454 A1 | 3/2011 | Dos Santos et al. | |
| 2011/0071456 A1 | 3/2011 | Rickard | |
| 2011/0113889 A1 | 5/2011 | Funken et al. | |
| 2011/0248671 A1 | 10/2011 | Santos et al. | |
| 2013/0116666 A1* | 5/2013 | Shih et al. | 604/891.1 |

FOREIGN PATENT DOCUMENTS

| | | |
|---|---|---|
| WO | WO 93/03665 | 3/1993 |
| WO | WO 98/03665 | 1/1998 |
| WO | WO 99/38470 A2 | 8/1999 |
| WO | WO 99/38470 A3 | 10/1999 |
| WO | WO 01/94784 | 12/2001 |
| WO | WO 03/001991 | 1/2003 |
| WO | WO 03/102632 | 12/2003 |
| WO | WO 2007/127305 A2 | 11/2007 |
| WO | WO 2007/136993 A1 | 11/2007 |
| WO | WO 2008/061043 A2 | 5/2008 |
| WO | WO 2008/061043 A3 | 9/2008 |
| WO | WO 2009/026499 | 2/2009 |
| WO | WO 2009/049686 | 4/2009 |
| WO | WO 2009/081031 A2 | 7/2009 |
| WO | WO 2009/081031 A3 | 9/2009 |
| WO | WO 2010/129446 A1 | 11/2010 |
| WO | WO 2011/034727 A1 | 3/2011 |
| WO | WO 2011/034738 A1 | 3/2011 |
| WO | WO 2011/034740 A1 | 3/2011 |
| WO | WO 2011/034742 A2 | 3/2011 |
| WO | WO 2011/035218 A1 | 3/2011 |
| WO | WO 2011/034742 A3 | 5/2011 |

OTHER PUBLICATIONS

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

International Searching Authority, Search Report and Written Opinion of the International Searching Authority, PCT/US2010/033329, Jul. 13, 2010, 14 pages.

International Searching Authority, Search Report and Written Opinion of the International Searching Authority, PCT/US2010/047429, Nov. 1, 2010, 15 pages.

International Searching Authority, Search Report and Written Opinion of the International Searching Authority, PCT/US2010/047600, Dec. 14, 2010, 13 pages.

International Searching Authority, Search Report and Written Opinion of the International Searching Authority, PCT/US2010/049424, Nov. 26, 2010, 15 pages.

International Searching Authority, Search Report of the International Searching Authority, PCT/US2011/036742, Aug. 17, 2011, 2 pages.

Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.

(56) References Cited

OTHER PUBLICATIONS

Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.

Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.

Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.

Schnakenberg, U., et al, "Initial Investigations on Systems for Measuring Intraocular Pressure," Sensors and Actuators, 2000, p. 287-291, vol. 85, Elsevier Science B.V., Germany.

Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.

Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.

Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.

Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May, 2002 DOI 10.1007/s00417-002-0474-y; pp. 335-336; Subject Collection Medicine.

International Searching Authority, Written Opinion of the International Searching Authority, PCT/US2010/047605, Dec. 16, 2010, 9 pages.

International Searching Authority, International Search Report of the International Searching Authority, PCT/US2010/047612, Dec. 21, 2010, 7 pages.

International Searching Authority, Written Opinion of the International Searching Authority, PCT/US2010/047612, Dec. 21, 2010, 10 pages.

Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.

Neagu Cristina R.; "A Medical Microactuator Based on an Electrochemical Principle"; Thesis at the Twente University,the Netherlands, Enschede; Aug. 28, 1998; pp. 1-162.

Saloomeh Saati MD., Ronalee L PhD, Po-Ying Li PhD, Ellis Meng PhD, Rohit Varma MD MPH, and Mark S. Humayun MD PhD; "Mini Drug Pump for Ophthalmic Use"; TRANS Am Ophthalmol Soc 2009; 107; pp. 60-71.

Erik Stemme and Goran Stemme; "A Valveless Diffuser/Nozzle-Based Fluid Pump"; ScienceDirect; Sensors and Actuators A, 39 (1993); pp. 159-167.

International Search Report and Written Opinion issued for PCT/US2013/026066, dated Apr. 17, 2013, 13 pages.

* cited by examiner

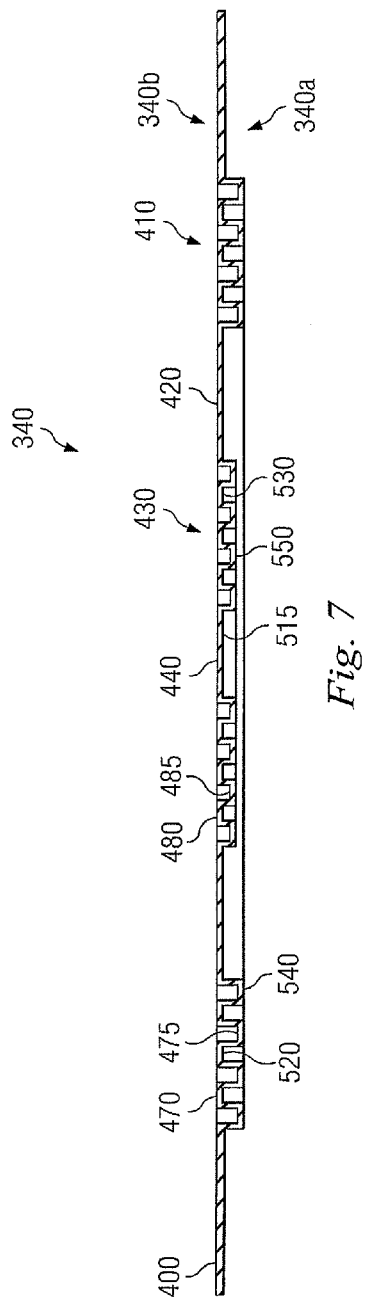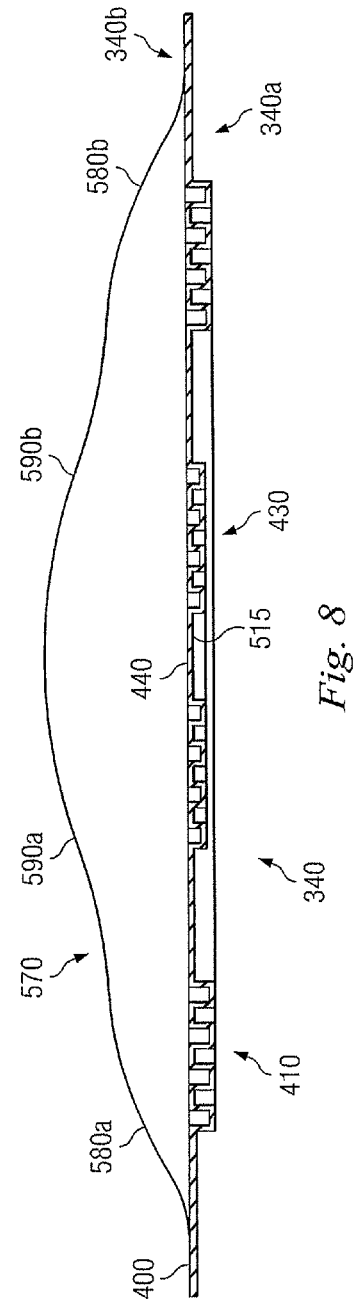

CORRUGATED MEMBRANE ACTUATORS

BACKGROUND

The present disclosure relates generally to valve actuators and associated systems and methods for use in ophthalmic treatments. In some instances, embodiments of the present disclosure are configured to be part of an IOP control system.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause an elevated IOP, which may lead to glaucoma. Aqueous fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. These devices are generally passive devices and do not provide a smart, interactive control of the amount of flow through the drainage tube. In addition, fluid filled blebs frequently develop at the drainage site. The development and over-pressurization of the bleb typically induces fibrosis, which leads to increased flow resistance and it is generally the case that this resistance increases overtime. This development and progression of fibrosis reduces or eliminates flow from the anterior chamber, eliminating the capacity of the drainage device to affect IOP. Conventional drainage devices often employ passive check valves that allow one-way fluid flow to the drainage site. Such valves have no mechanism for controlling over-pressurization within the bleb, which may increase to unacceptable levels with over-drainage of aqueous humor into the bleb.

The devices, systems, and methods disclosed herein overcome one or more of the deficiencies of the prior art.

SUMMARY

This disclosure relates generally to implantable systems for controlling intraocular pressure (IOP) utilizing a membrane valve and a shaped membrane.

In one example, IOP control systems or implants utilize membrane valve actuators to affect flow through a drainage device. Such membrane valve actuators utilize membranes that deflect in response to various pressure differentials, allowing flow across the valve to regulate intraocular pressure (IOP). When flat membrane valve actuators are subjected to a force or pressure, the deflection of the membrane reflects the magnitude of the force or pressure. The deflection of the flat membrane is generally linear with the applied force or pressure as long as the deflection is a small fraction of the thickness of the flat membrane. As the force or pressure increases beyond this point, however, the deflection becomes a non-linear function of the applied force or pressure due to stretching of the flat membrane. Therefore, flat membrane actuators have limited degrees of freedom available to generate useful membrane deflection profiles. In general, to achieve a predictable deflection profile, either large pressure differentials, very thin membranes, or very large membranes may be required. The implantable IOP control systems disclosed herein utilize corrugated membrane actuators that offer the ability to fine tune membrane deflection or response to pressure differentials, thereby increasing the degree of controllability of valve actuation allowing flow across the valve through the drainage device and, consequently, facilitating greater control over the patient's IOP.

In one exemplary aspect, the present disclosure is directed to an IOP control valve for implantation in an eye of a patient comprises a housing and a corrugated membrane. The housing may include a fluid inlet and a fluid outlet. The corrugated membrane may be anchored within the housing to form a reference chamber on a first side of the corrugated membrane and a fluid flow channel on a second opposing side of the membrane. The reference chamber may have a reference chamber pressure representative of atmospheric pressure. The fluid flow channel may selectively increase and decrease in size to permit fluid to flow from the fluid inlet to the fluid outlet, and the corrugated membrane may be configured to affect flow through the fluid flow channel from the fluid inlet to the fluid outlet by deflecting in response to pressure differentials of the reference chamber pressure and the fluid flow channel pressure acting on the opposing sides of the corrugated membrane.

In another exemplary embodiment, the present disclosure is directed to an IOP control valve for implantation in an eye of a patient comprises a drainage tube configured to convey aqueous humor from an anterior chamber of the eye and a pressure-driven membrane valve in fluid communication with the drainage tube. The membrane valve includes a membrane, and may be actuatable in response to pressure differentials. The membrane may be configured to control flow rates of the aqueous humor along the drainage tube by deflecting in response to pressure differentials acting on the membrane.

In another exemplary embodiment, the present disclosure is directed to a method of regulating pressure by adjusting drainage from an anterior chamber of an eye with a membrane valve. The method includes directing fluid through a fluid flow channel and modifying the amount of drainage through the membrane valve in response to pressure acting on the flexible membrane. The fluid flow channel may be formed in part by a flexible membrane shaped with at least one corrugation including a peak, a valley, and a sidewall extending at a first angle between the peak and the valley. Modifying the amount of drainage through the valve may occur by deflecting the membrane to change the first angle modifying the amount of drainage through the membrane valve in response to pressure acting on the flexible membrane by deflecting the membrane to change the first angle to a second, different angle relative to the peak and valley, and to increase or decrease the size of the fluid flow channel in the membrane valve.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 7 is a cross-sectional side view of the membrane actuator shown in FIG. 5 according to an embodiment of the present disclosure.

FIG. 8 is a diagrammatic representation of an exemplary membrane deflection of the membrane actuator shown in FIG. 7 according to an embodiment of the present disclosure.

DETAILED DESCRIPTION OF THE PREFERRED EMBODIMENTS

Figure 1:
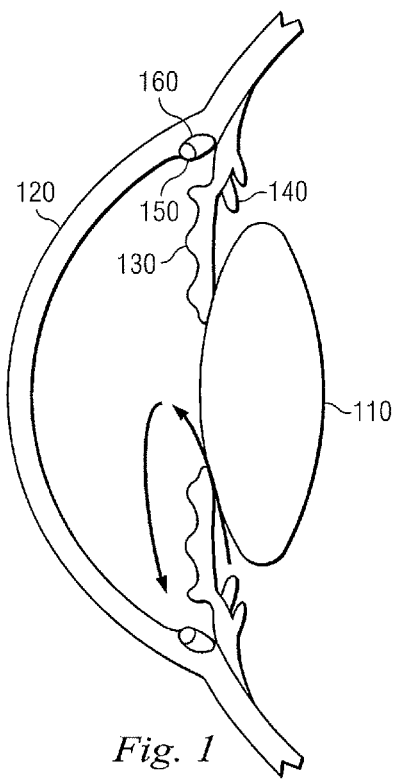
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to corrugated membrane actuators used in the operation of valves. In some instances, embodiments of the present disclosure are configured to be part of an IOP control system. The membrane actuators disclosed herein include corrugations designed to extend the linear range of the membrane in response to pressure differentials across the membrane, thereby providing a greater degree of control over the membrane deflection profile than that provided by an uncorrugated, flat membrane. The incorporation of corrugations in the membrane allows the membrane to unfold as the pressure differential increases. Thus, the corrugated membrane actuators disclosed herein may reduce the influence of the intrinsic material stress of the membrane (e.g., thermal and packaging stresses determined by the membrane fabrication process) and alter the compliance of the membrane to increase the mechanical sensitivity of the membrane. Moreover, the combination of deep and shallow corrugations may be optimized to provide a particular physical deflection profile as a function of the pressure differentials across the membrane.

Figure 2:
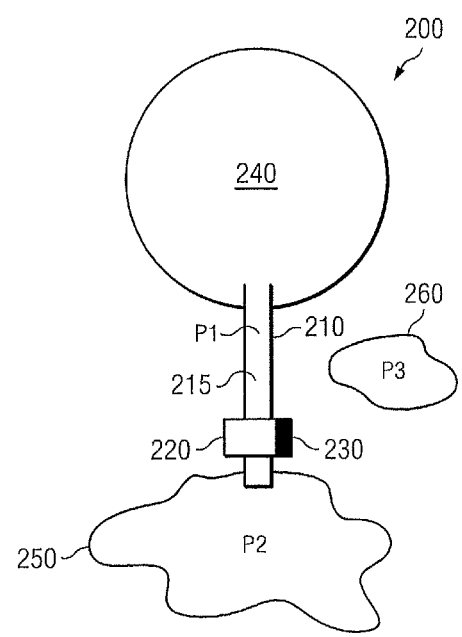
FIG. 2 is a schematic diagram of an exemplary IOP control system according to an embodiment of the present disclosure.

FIG. 2 is a diagram of an exemplary IOP control system 200, including a drainage tube 210, a valve system 220, and a divider 230. In the embodiment pictured in FIG. 2, the IOP control system 200 is arranged in the eye such that three areas of pressure interact with the IOP control system 200: P1, P2, and P3. Pressure area P1 reflects the pressure of the anterior chamber 240, pressure area P2 reflects the pressure of a drainage site in the subconjunctival space (and may reflect bleb pressure), and pressure area P3 reflects a pressure located remotely from P1 and P2 (effectively reflecting atmospheric pressure). In some embodiments, pressure area P1 reflects the pressure located in a lumen or tube that is in fluidic communication with the anterior chamber 240.

The drainage tube 210 drains aqueous humor from the anterior chamber 240 of the eye. The valve system 220 controls the flow of aqueous humor through the lumen 215 of the tube 210. In the embodiment shown, the pressure area P1 reflects the pressure in the lumen 215 upstream from the valve system 220 and downstream from the anterior chamber 240. In this manner, pressure area P1 reflects the pressure in the anterior chamber 240. The expected discrepancy between the true anterior chamber pressure and that reflected by area P1 when located in a tube downstream of the anterior chamber 240 (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

In some embodiments, a divider 230 separates pressure areas P1 and P2 from pressure area P3. Pressure area P2 reflects the pressure at a drainage site. As such, pressure area P2 may be located in a pocket, such as a bleb, that generally contains aqueous humor or in communication with such a pocket, via a tube, for example, and is in a wet location. Pressure area P3 is physically separated from both pressure area P1 and pressure area P2 by the divider 230. The divider 230 is a physical structure that separates and isolates the pressure area P1 and the wet drainage site 250 of pressure area P2 from the (relatively) dry location 260 of pressure area P3. In some embodiments, the divider 230 includes the physical components of the valve system 220, such as parts of a housing. Note that the divider 230 may take many forms, such as, but not limited to, a tube fluidically coupling pressure area P3 to a remote site or a pocket away from and fluidically independent of the drainage site.

In some embodiments of the present disclosure, the atmospheric pressure area P3 reflects the pressure in an area in close proximity to the eye, and in one embodiment, the pressure area P3 may reflect the pressure in the eye under the conjunctiva. In such cases, pressure area P3 reflects a pressure that can be correlated with atmospheric pressure. Pressure area P3 may also reflect the pressure of a (relatively) dry portion 260 of the subconjunctival space, separate and apart from the drainage site 250. Regardless of location, pressure area P3 is intended to reflect atmospheric pressure in the vicinity of the eye or at the eye's surface.

Generally, IOP is a gauge pressure reading—the difference between the absolute pressure in the eye (as reflected by P1) and atmospheric pressure (as reflected by P3). Atmospheric pressure, typically about 760 mm Hg, often varies in magnitude by 10 mmHg or more depending on weather conditions or indoor climate control systems. In addition, the effective atmospheric pressure can vary significantly—in excess of 100 mmHg—if a patient goes swimming, hiking, riding in an airplane, etc. Such a variation in atmospheric pressure is significant since IOP is typically in the range of about 15 mm Hg. Thus, for accurate control of IOP, it is desirable to have an IOP control system reactive to the pressure differential across the pressure of the anterior chamber (as reflected by P1) and atmospheric pressure in the vicinity of the eye (as reflected by P3). Therefore, in one embodiment of the present disclosure, the IOP control system 200 reacts to the pressure differential across P1 and P3 continuously or nearly continuously so that the actual IOP (as P1−P3 or P1−f(P3)) can be responded to accordingly.

The valve system 220 is connected to the drainage tube 210 and regulates the flow of aqueous humor through the lumen 215 of the tube 210 from the anterior chamber 240 to the drainage site 250. The valve system 220 is disposed along, and may form a part of, the drainage tube 210 between the anterior chamber 240 and the drainage site 250. In some embodiments, the valve system 220 is disposed within the lumen 215 of the drainage tube 210. The valve system 220 is configured to regulate the flow of fluid through the drainage tube 210, and thereby control pressure in the eye, including the IOP. For example, when the IOP is high, the valve system 220 may operate to permit increased flow through the drainage tube 210, and when IOP is low, the valve system 220 may operate to decrease the flow through the drainage tube 210. In the embodiment pictured in FIG. 2, the valve system 220 is configured to be continuously responsive to various pressure differentials (P1−P3 or P2−P3) and control fluid flow to the drainage site 250. It is important to note that the corrugated membranes disclosed herein may also be used in electrolysis membrane valves, which respond similarly to a pressure differential though the electrolysis process is used to control pressure on one side of the valve.

The valve system 220 includes at least one pressure-driven membrane valve that does not require external power or feedback from electronic pressure sensors to operate. In the embodiment shown in FIG. 3, a pressure-driven membrane valve 300 includes a housing 310, a reference chamber 320, a valve seat 330, a fluid flow channel 335, a corrugated membrane 340, and an optional boss member 350. The valve 300 is configured to allow or block aqueous humor flowing from the anterior chamber 240 through the drainage tube 210 to any subsequent valves within the valve system 220 or to the drainage site 250. In the pictured embodiment, the components of the valve 300 are generally circular in geometry and are symmetric about the center line AA. In alternative embodiments, different geometries for the valve are contemplated, including ovoid and rectangular geometries, for example.

The housing 310 is defined by a housing section 360 and a housing section 370, which mate with one another to form an enclosure within which various other components of the valve 300, such as the corrugated membrane 340, the valve seat 330, and the boss member 350, are positioned. The housing section 370 includes a fluid inlet 380, a fluid outlet 390, and the valve seat 330. The valve seat 330 is positioned between the fluid inlet 380 and the fluid outlet 390 such that fluid flows from the fluid inlet 380, through the fluid flow channel 335, and to the fluid outlet 390. In alternative embodiments, the housing 310 may be integrally formed of the two sections 360, 370. In alternative embodiments, the housing sections 360, 370 may cooperate to form the fluid inlet 380 and the fluid outlet 390. The housing 310 may be constructed of any suitable biocompatible material, provided the material is able to maintain constructional integrity at high internal pressures and withstand pressure changes.

The reference chamber 320 is bounded and defined by at least the housing section 360 and the corrugated membrane 340. The reference chamber 320 is in communication with pressure area P3, which is expected to reflect the atmospheric pressure. In some embodiments, the reference chamber 320 is in communication with the dry subconjunctiva. In alternative embodiments, the reference chamber 320 interfaces with another portion of the eye or to atmospheric pressure directly. Moreover, in alternative embodiments, a plurality of membranes using separate reference chambers (and reference chamber pressures) is contemplated for use in the valve 300.

In some embodiments, the valve seat 330 may be a floor surface of the housing section 370. In the pictured embodiment, the boss member 350 is positioned on the valve seat 330 such that the boss member concentrically overlies the fluid inlet 380. It should be noted that some contemplated embodiments do not include the boss member 350. In a valve without a boss member, the central aperture of the valve seat 330 serves as the entrance to the fluid flow channel 335. In a valve without a boss member, the valve seat is shaped and configured such that when the corrugated membrane 340 rests on the valve seat 330, the valve 300 is in a closed condition.

Figure 3:
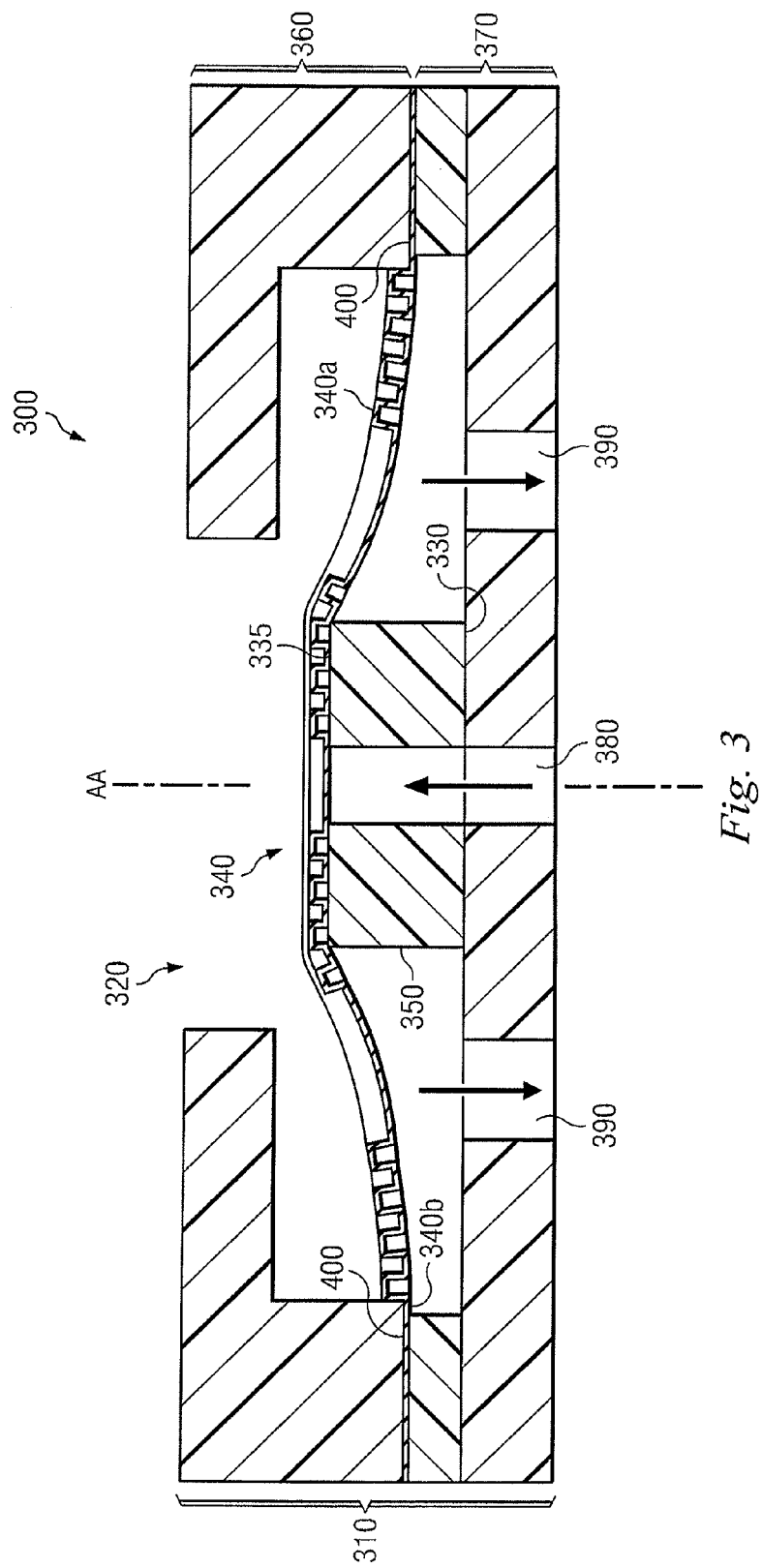
FIG. 3 is a schematic cross-sectional diagram of an exemplary pressure-driven membrane valve in a closed condition according to an embodiment of the present disclosure.

In the pictured embodiment in FIG. 3, the valve 300 includes a boss member 350 shaped and configured as a generally annular or toroid component. The boss member 350 is shaped and configured such that when the corrugated membrane 340 rests on the boss member 350, the valve 300 is in a closed condition. The boss member 350 is positioned over the valve seat 330 such that the central apertures of the boss member 350 and the valve seat 330 are co-aligned about the central axis AA. The boss member 350 is positioned on the valve seat 330 such that the boss member 350 effectively functions as the valve seat, albeit at a raised position within the housing 300. Thus, in the embodiment pictured in FIG. 3, the central aperture of the boss member 350 serves as both the exit of the fluid inlet 380 and the entrance to the fluid flow channel 335, and when the flow control member 340 rests on the boss member 350, the valve 300 is in a closed position. The boss member 350 permits increased design flexibility and flow control for the valve 300. Varying the height and other dimensions of the boss member 350 affects the amount and rate of fluid flow through the valve 300. In various embodiments, the boss member 350 may be configured as an integral extension of the valve seat 330, or may be a separate component. In some examples, the boss member 350 is an integral portion of the valve seat 330 and may be molded or machined at the same time as the valve seat 330.

The fluid flow channel 335 comprises the circumferential gap that arises between the boss member 350 (or, in embodiments without a boss member, the valve seat 330) and the corrugated membrane 340 when the flow control member 340 deflects away from the boss member 350 toward the reference chamber 320. As shown in FIG. 3, the fluid flow channel 335 is a potential space or gap when the corrugated membrane 340 rests on the boss member 350 and the valve 300 is in a closed condition. As shown in FIG. 3, however, the fluid flow channel 335 enlarges when the corrugated membrane deflects off the boss member 350 into the reference chamber 320 and the valve 300 is in an open condition. When the valve 300 is in an open condition, the fluid flow channel 335 is generally an approximate constant width around the annular sealing surface of the boss member 350 (i.e., the gap between the boss member 350 and the membrane 340 is generally uniform for a given pressure differential) at any given time.

The corrugated membrane 340 comprises a flexible, deformable, fluid-tight membrane or diaphragm that provides valve functionality by deflecting in response to pressure differentials across its two opposing sides. The corrugated membrane 340 includes two generally parallel surfaces, a surface 340a and an opposite surface 340b. The surface 340a faces the reference chamber 320, and consequently conveys the pressure of pressure area P3. The surface 340b faces the drainage tube 210, and in particular the fluid inlet 380, and consequently conveys the pressure of pressure area P1. The surface 340b of the corrugated membrane 340 is configured to selectively seal against the boss member 350 and thereby close the valve 300 when the pressure against the surface 340a sufficiently outweighs the pressure against the surface 340b. As will be explained in further detail below, the flow control member 340 deflects in response to pressure differences between the fluid inlet 380 and the reference chamber 320 to at least partially open and close the valve 300 by changing the dimensions of the fluid flow channel 335.

As shown in FIG. 3, the corrugated membrane 340 is securely held in place within the housing 310 so that it will not be displaced by the force of the fluid flowing through the valve 300. In the embodiment pictured in FIG. 3, the corrugated membrane 340 is anchored between the housing section 360 and the housing section 370. A valve 300 having this configuration is designed for use in a scenario where the pressure in the reference chamber 320 (P3) is generally lower than the pressure in the fluid in the drainage tube 210 (P1), where P1–P3 ranges from approximately 5 to 30 mmHg. More specifically, a peripheral zone 400 of the corrugated membrane 340 is sandwiched between the walls of the housing section 360 and the walls of the housing section 370. The housing section 360, the membrane 340, and the housing section 370 are secured into this arrangement by any of a variety of known methods, including adhesive, welding, or mechanical fasteners, for example. Regardless of how the membrane 340 is secured within the housing 300, at least a portion of the housing 300 applies a compressive force to a periphery of the membrane 340 to maintain it in a desired position relative to the valve seat 330 or boss member 350.

The valve 300 is configured as a throttle valve that can completely or partially block the flow of aqueous humor by deflecting the corrugated membrane 340 completely or partially across the fluid inlet 380. The housing 310 is configured to connect with drainage tube 210 such that deflection of the corrugated membrane 340 at least partially opens and closes the lumen 215 to the outflow of aqueous humor. As described above, the position of the flow control member 340 determines whether the valve 300 is in an open or closed condition. When the membrane 340 seals against the boss member 350, the valve 300 is in a closed condition. When the membrane 340 deflects away from the boss member 350, the valve 300 is in an open condition.

The valve 300 is in fluidic communication with the drainage tube 210 and in communication with the dry subconjunctiva. In particular, the fluid inlet 380 fluidly interfaces with the drainage tube 210 (reflecting pressure area P1) and the reference chamber 320 interfaces with the dry subconjunctiva (reflecting pressure area P3). The corrugated membrane 340 extends across the housing 310 to form a sealed separation between the reference chamber 320 and the fluid inlet 380, thereby creating an effective separation between pressure areas P3 and P1, respectively. Accordingly, as the pressure increases against one side of the corrugated membrane 340, the pressure increase acts to deflect the corrugated membrane 340 in the direction away from the higher pressure. The fluid inlet 380 conveys the pressure of pressure area P1 on one surface 340b of the corrugated membrane 340. The reference chamber 320 conveys the pressure of pressure area P3 on the opposite surface 340a of the corrugated membrane 340.

As mentioned above, the corrugated membrane 340 directs flow by deflecting within the housing 310 of the valve 300 in response to the pressure differential between the fluid chamber pressure (as reflected by pressure area P1) against one surface 340b of the corrugated membrane 340 and the dry subconjunctival pressure (as reflected by pressure area P3, which is expected to correspond to atmospheric pressure) against the opposite surface 340a of the corrugated membrane 340. As it deflects, the membrane 340 increases and decreases the size of the fluid flow channel 335. The size of the fluid flow channel 335 affects the rate of flow and the pressure drop across the valve. Accordingly, for larger pressure differentials, the fluid flow channel is larger and for smaller pressure differentials the fluid flow channel is smaller.

The cracking pressure of the valve 300 is the pressure threshold above the pressure of the reference chamber 320 (P3) at which the membrane 340 deflects off the boss member 350. In particular, if the IOP exceeds the cracking pressure of the corrugated membrane 340, then the valve 300 will assume an open condition and allow flow to regulate the IOP down to the desirable range. Otherwise, the valve 300 remains in a closed condition because the IOP (P1–P3) or pressure difference across the membrane 340 is below the cracking pressure.

The cracking pressure of the valve 300 and the deflection profile of the corrugated membrane 340 are dependent on the structure of the valve housing 310 as well as the material composition, size, stiffness, and structure (including, by way of non-limiting example, the depth, number, and arrangement of corrugations) of the corrugated membrane 340. Accordingly, the cracking pressure may be preselected by controlling these parameters during the fabrication, manufacturing, or assembly processes. In one example, these parameters are selected so that the valve 300 remains closed when the IOP (P1–P3) is below the desired cracking pressure. After implantation of the valve 300, the patient's IOP generally begins to approximate the cracking pressure of the valve 300. Therefore, the surgeon may select a valve 300 having a particular cracking pressure based on the most appropriate or desired IOP range for the treatment of a particular condition.

Figure 4:
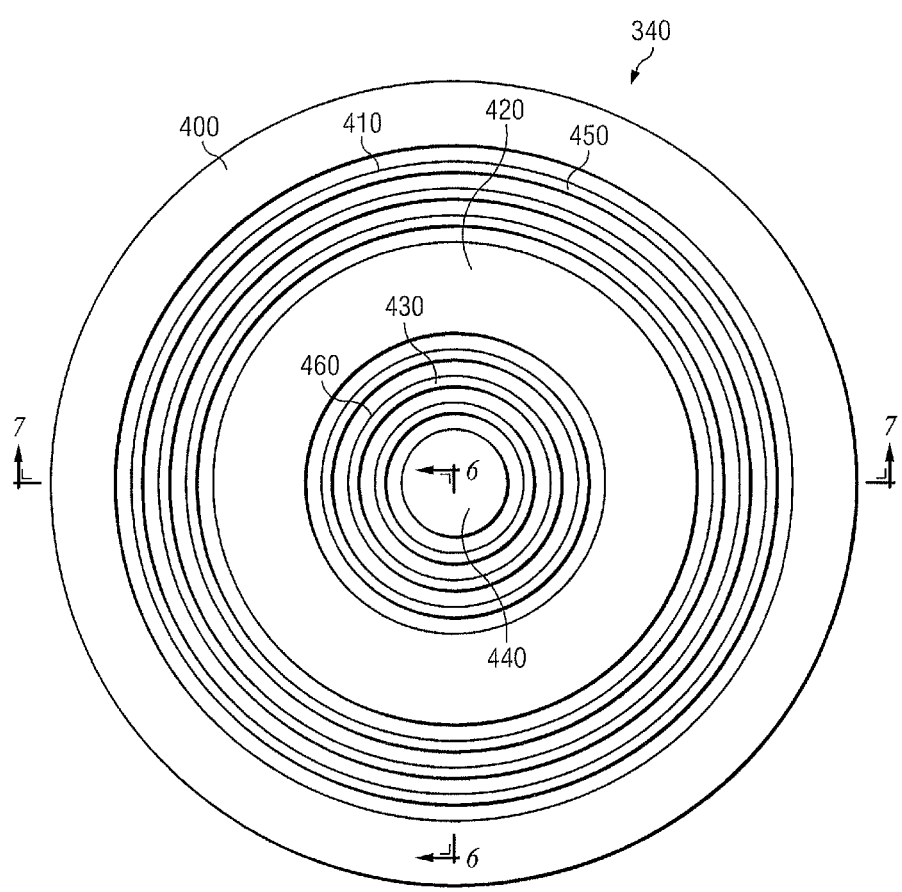
FIG. 4 is a bottom plan view of the membrane actuator shown in FIG. 4 according to an embodiment of the present disclosure.

FIG. 4 illustrates the surface 340b in a bottom plan view of the corrugated membrane 340 according to one embodiment of the present disclosure. In the pictured embodiment, the corrugated membrane 340 is shaped and configured as a corrugated, substantially planar membrane having a circular shape. Other shapes are also contemplated for the membrane 340, including, but not by way of limitation, rectangular or ovoid shapes. The shape of the corrugated membrane 340 may be chosen depending upon spatial, pressure drop, material, and flow rate constraints. The corrugated membrane 340 is shaped and configured to define the peripheral zone 400, a deep corrugation zone 410, an intermediate zone 420, a shallow corrugation zone 430, and a central zone 440. The deep corrugation zone 410, which surrounds the intermediate zone 420 and is bounded by the peripheral zone 400, includes a plurality of concentric deep corrugations 450. The shallow corrugation zone 430, which surrounds the central zone 440 and is bounded by the intermediate zone 420, includes a plurality of concentric shallow corrugations 460. As mentioned above with reference to FIG. 3, the peripheral zone 400 of the corrugated membrane 340 is shaped such that it may be sandwiched between the walls of the housing section 360 and the walls of the housing section 370 to anchor the membrane 340 within the housing 310.

Though the corrugations 450, 460 are shaped and configured as concentric circles or rings, the corrugations are not limited to a particular shape or to a particular combination of shapes. Exemplary shapes for the corrugations 450, 460 include both open and closed shapes. Exemplary open shapes include, by way of non-limiting example, linear or straight shapes such as straight lines of varying lengths, and curved shapes, such as half-circles, crescents, and partial ellipses. Exemplary closed shapes include, by way of non-limiting example, circles, rectangles, triangles, and squares.

Figure 5A:
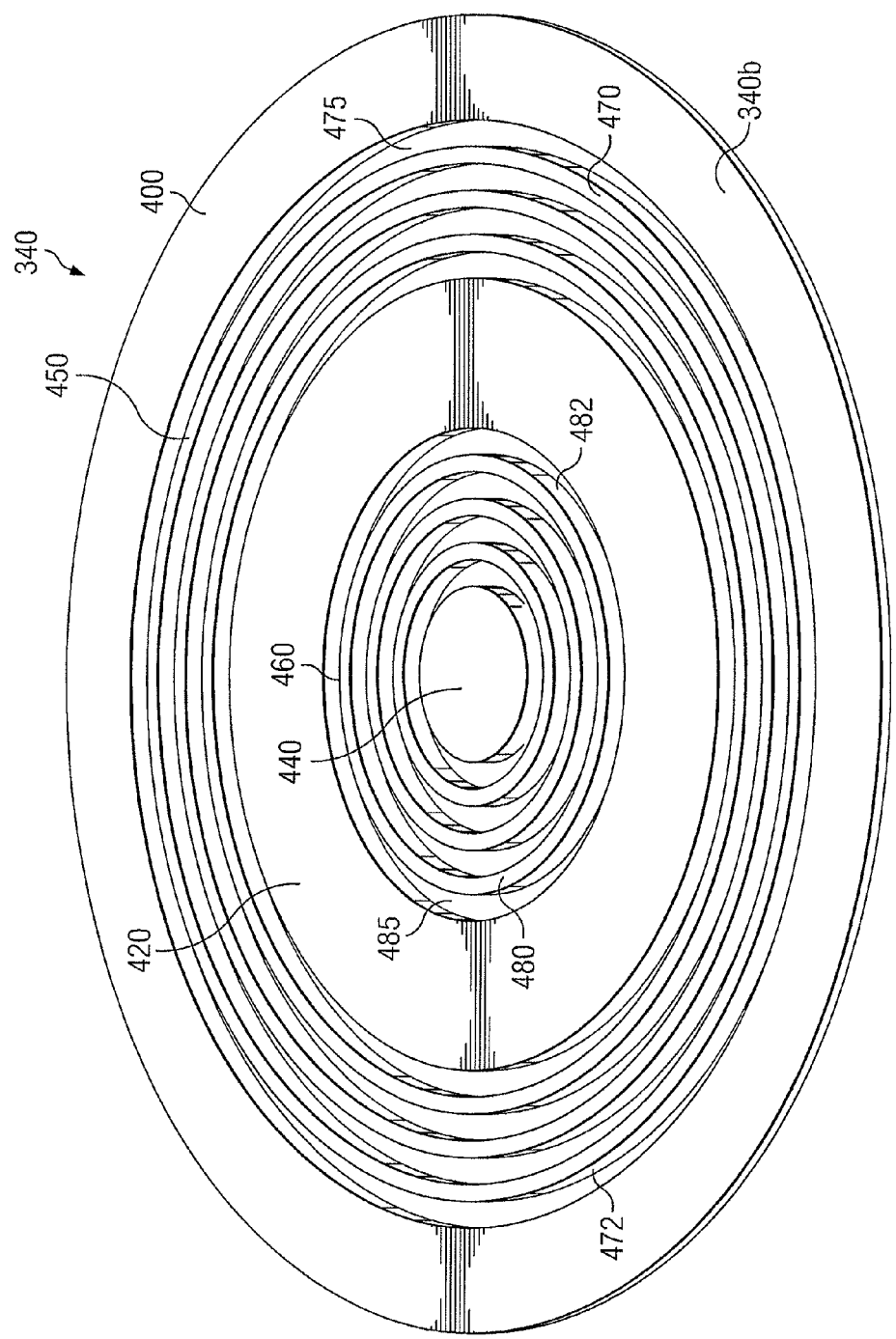
FIGS. 5a and 5b are perspective views of opposite surfaces of an exemplary membrane actuator useable in a pressure-driven valve according to an embodiment of the present disclosure.

FIG. 5a illustrates a perspective view of the corrugated membrane 340 depicted in FIG. 4 and shows the deep corrugations 450 and shallow corrugations 460 on the surface 340b. The corrugations 450, 460 include alternating peaks (or ridges) and valleys (or grooves) connected by sidewalls within the membrane 340. The peaks comprise raised plateaus in the corrugations, and the valleys comprise the bases of channels in the corrugations. Each corrugation includes a peak connected by a sidewall to a neighboring valley and another sidewall. Thus, each corrugation includes a peak, a valley, and two sidewalls. In particular, the deep corrugations 450 include deep peaks 470, deep sidewalls 472, and deep valleys 475. The shallow corrugations 460 include shallow peaks 480, shallow sidewalls 482, and shallow valleys 485.

Though the pictured surface 340b includes three deep peaks 470, four deep valleys 475, three shallow peaks 480, and four shallow valleys 485, the corrugation zones 410, 430 are not limited to a particular number of peaks and valleys. Moreover, the corrugated membrane is not limited to a particular number or arrangement of corrugation zones, and nor is the arrangement between shallow and deep corrugations limited. The combination of deep and shallow corrugations may be optimized to provide a particular physical deflection profile as a function of the pressure differentials across the membrane.

Figure 10:
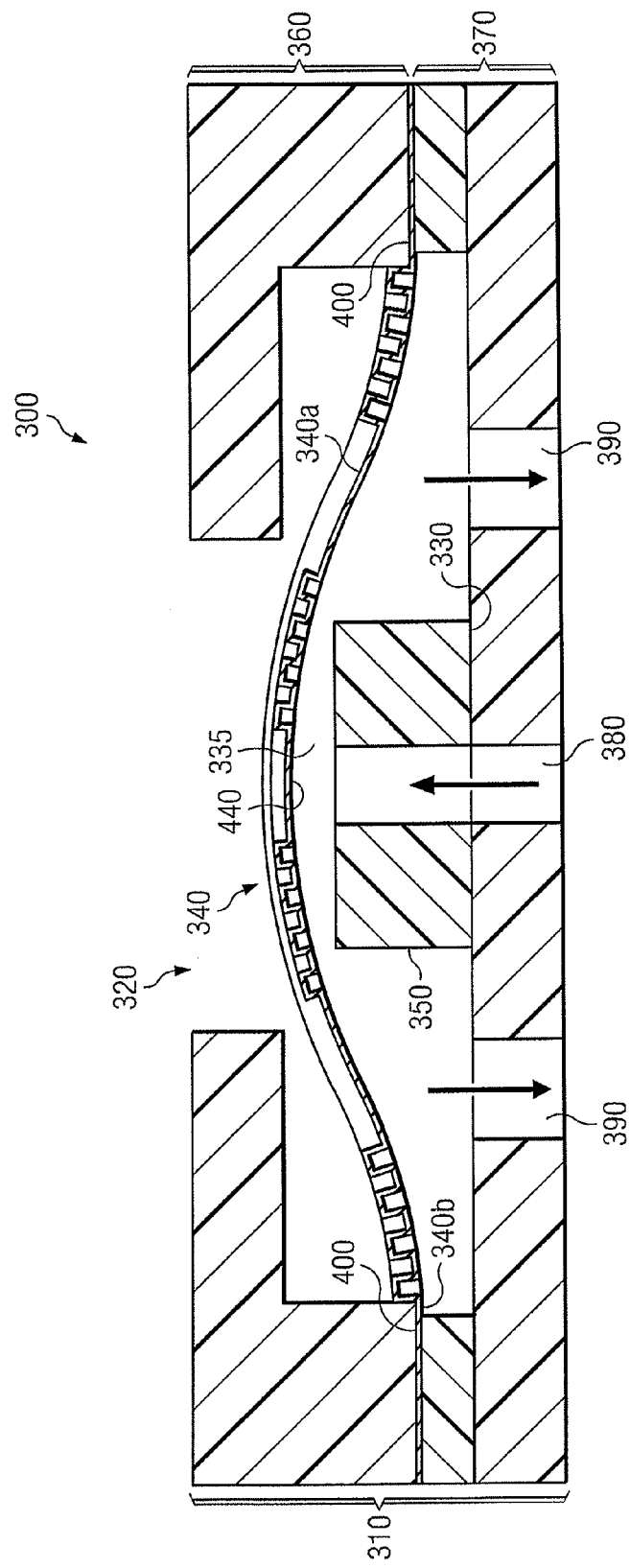
FIG. 10 is a schematic cross-sectional diagram of the pressure-driven membrane valve shown in FIG. 3 in an open condition according to an embodiment of the present disclosure.

The central zone 440 is shaped and configured to contact and form a transient seal against the fluid inlet 380 when the corrugated membrane 340 is operative in a valve 300. For example, in the pictured embodiment in FIG. 3, the central zone 440 is shaped and configured to contact the boss member 350 when the membrane deflects toward the fluid inlet 380. In valve embodiments lacking a boss member 350, the central zone 440 is shaped and configured to contact the valve seat 330 when the membrane deflects toward the fluid inlet 380. In some embodiments, the central zone 440 is sized to have the same diameter as the diameter of the fluid inlet 380 (i.e., the central opening of either the boss member or the valve seat). In other embodiments, the central zone 440 is sized to have a larger diameter than the diameter of the fluid inlet 380 (as shown in FIG. 10). In other embodiments, the central zone 440 is sized to have a smaller diameter than the diameter of the fluid inlet 380.

In some embodiments, the central zone may comprise a raised or bossed portion of the membrane configured to seal against the boss member 350 (or the valve seat 330) when the membrane deflects toward the fluid inlet 380. In some embodiments, the central zone is shaped and sized to seat within a central orifice of the boss member 350 (or the valve seat 330) when the membrane deflects toward the fluid inlet 380. The bossed portion may permit increased design flexibility and flow control for the valve 300. Varying the height and other dimensions of the central zone affects the amount and rate of fluid flow through the valve 300. In various embodiments, the bossed portion of the central zone may be configured as a separate component from the membrane 340. In other embodiments, the bossed portion may be an integral extension of the central zone 440.

Figure 5B:
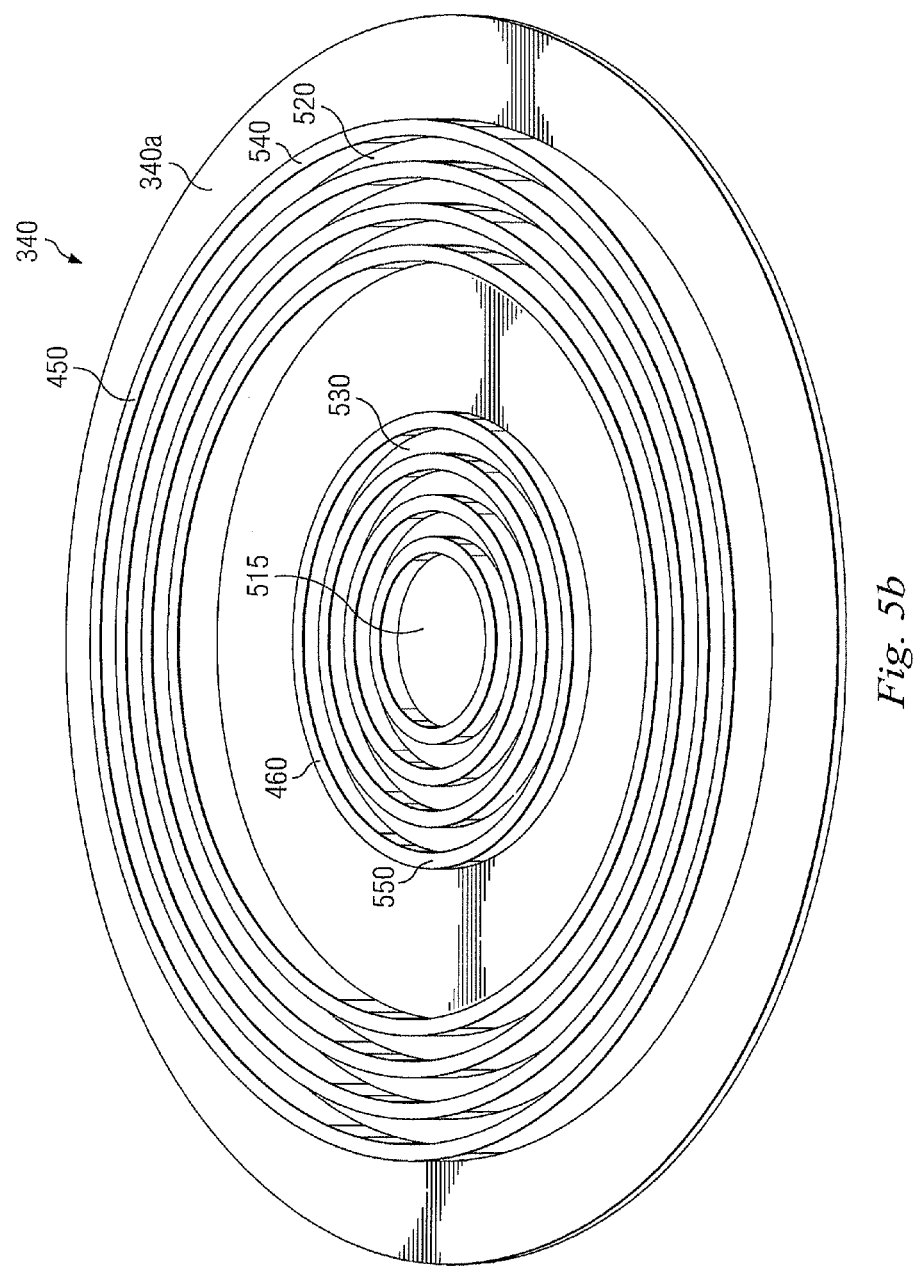

FIG. 5b illustrates a perspective view of the corrugated membrane 340 depicted in FIG. 4 and shows the deep corrugations 450 and the shallow corrugations 460 on the surface 340a. The surface 340a includes a central depression 515, which is the opposite side of the central zone 440 on the surface 340b. The surface 340a include peaks and valleys which are "in-phase" and parallel with the peaks and valleys of the surface 340b. In other words, the peaks 470, 480 of the surface 340b directly overlie valleys 520, 530, respectively, of the surface 340a, and the valleys 475, 485 of the surface 340b directly overlie peaks 540, 550, respectively, of the surface 340a. Thus, the pictured surface 340a includes four deep peaks 540, three deep valleys 520, four shallow peaks 550, and three shallow valleys 530. Other embodiments may include corrugations on either side of the membrane that are "out-of-phase," i.e., the peaks on one side directly overlie the peaks on the other side, or the corrugations on one side are crisscrossed or non-parallel relative to the corrugations on the opposite side.

Figure 6A:
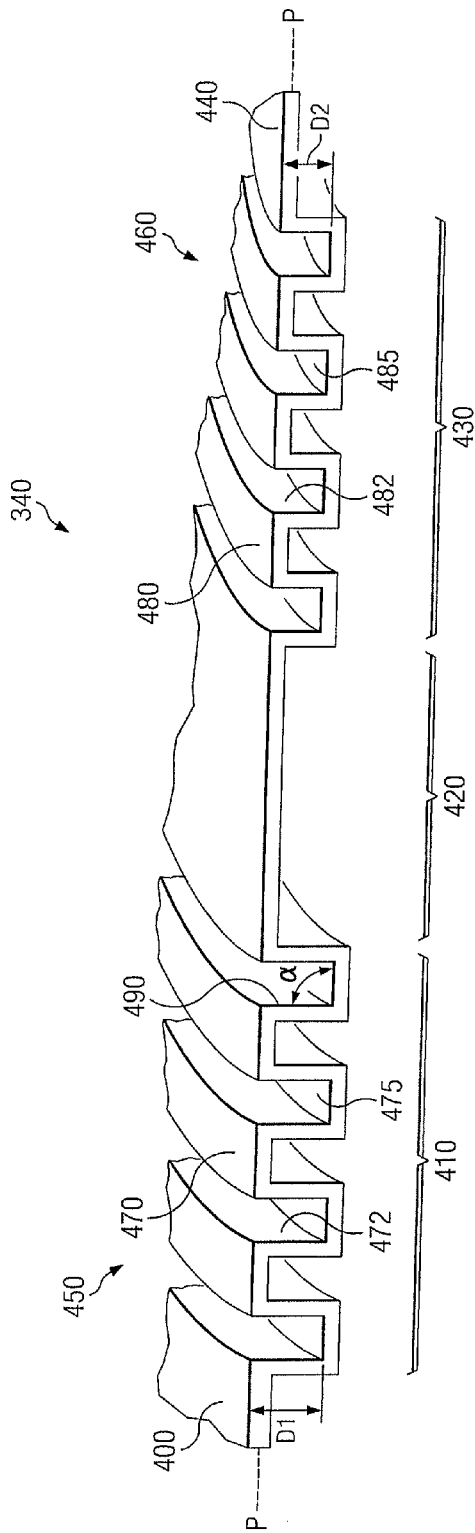
FIG. 6a is a cross-sectional perspective view of certain corrugations in the membrane actuator shown in FIG. 4 according to an embodiment of the present disclosure.

FIG. 6a illustrates a perspective view of a cross-section of a portion of the membrane 340 shown in FIG. 4 taken along the line 6a-6a. As shown in FIG. 6a, the peripheral zone 400 is disposed in substantially the same plane P as the central zone 440 when the membrane 340 is at rest. In embodiments including a raised or bossed central zone, the central zone will not be disposed in substantially the same plane P as the peripheral zone 400. The plurality of concentric corrugations 450, 460 are arranged in a periodic configuration. In particular, each corrugation extends downwards from a peak along a sidewall to a neighboring valley and extends upwards from the valley along an adjacent sidewall to a neighboring peak to complete the periodic configuration of the corrugation.

In the pictured embodiment, when the membrane 340 is substantially flat, as shown in FIG. 6a, the sidewalls extend between neighboring peaks and valleys at an angle α. In other embodiment, the sidewalls may extend from the peaks and valleys at any of a variety of angles α, including by way of non-limiting example acute, right, and obtuse angles. For example, in the pictured embodiment, the deep sidewalls 472 extend from the peaks 470 to the valleys 475 at right angles. As the membrane 340 deflects, the angle α between the sidewalls and the peaks and valleys may change. In essence, the corrugated membrane deflects by unfolding like an accordion, as opposed to merely stretching, although some embodiments are configured to stretch under pressure. The membrane deflects as a response to a pressure differential acting on the flexible membrane. Specifically, the pressure differential generates deflection by a change of the angle α from a first angle to a second, different angle relative to the peak and valley increase or decrease the size of the fluid flow channel in the membrane valve.

In the embodiment pictured in FIG. 6a, the shallow corrugations 460 closer to the central zone 440 are of lower depth or amplitude than the deep corrugations 450 closer to the peripheral zone 400. The deep corrugations 450 are shaped and configured to have a greater depth D1 than a depth D2 of the shallow corrugations 460. The depths D1, D2 comprise the height of the corresponding sidewalls 472, 482. Thus, the depths D1, D2 reflect the vertical distance between neighboring peaks and valleys. The depths D1, D2 of the corrugations 450, 460, respectively, are not limited to any particular depth. In some embodiments, the depth D1 may range from 5 to 50 μm and the depth D2 may range from 2 to 30 μm. In various other embodiments, the membrane 340 may include corrugations having any pattern of depths. For example, certain embodiments may include corrugations having varying depths within individual zones, or may include corrugation zones having identical depths (as opposed to deep and shallow depths). In yet other embodiments, the corrugations located closer to the central zone 440 may be of higher amplitude and depth than the corrugations closer to the peripheral zone 400.

Figure 6C:
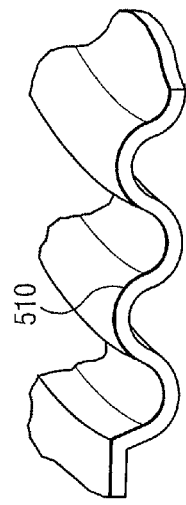
FIG. 6c is a cross-sectional perspective view of exemplary corrugations in a membrane actuator according to another embodiment of the present disclosure.
Figure 6B:
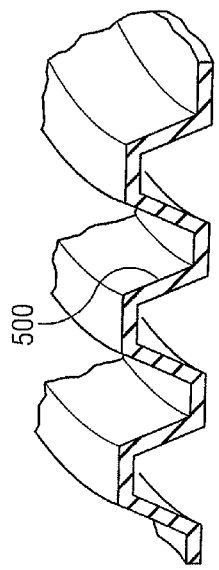
FIG. 6b is a cross-sectional perspective view of certain exemplary corrugations in a membrane actuator according to another embodiment of the present disclosure.

In FIG. 6a, the corrugations 450, 460 are shaped to include rectangular or squared off edges 490. Various other embodiments may include edges of any of a variety of shapes, including, by way of non-limiting example, rounded and trapezoidal, such as acutely or obtusely angled edges. For example, FIG. 6b illustrates corrugations including obtusely angled edges 500, and FIG. 6c illustrates corrugations including rounded edges 510.

The corrugated membrane 340 may be unitarily made or formed by vapor deposition, stamping, molding, or any other suitable means known in the art from any suitable biocompatible, flexible material. The membrane 340 can be constructed of any suitable biocompatible material that can move, flex, deform, or deflect in response to differential pressures. The material may comprise a thermoplastic material, an elastomeric material, or a thermoplastic elastomer. In some embodiments, the corrugated membrane 340 is constructed of a micro-electromechanical system (MEMS) membrane, such as, but not by way of limitation, a Parylene membrane. Parylene is a biocompatible, inert, and nondegradable material that is commonly used to fabricate mechanically robust microstructures. MEMS membranes are easier to deflect (i.e., they have a larger throw at a lower pressure) with increasingly compliant material, increasingly thin membranes, and increasingly large radii or lengths. In addition to being actuatable by pressure differentials, MEMS membranes may also be actuated by several other means, including, but not by way of limitation, electrostatically, magnetically, and thermally.

For purposes of practicality, the corrugated membrane 340 should be thick enough to be durable and resistant to corrosion and leakage. However, the membrane 340 should also be thin enough to provide the necessary flexibility and deflection capabilities which are required in a substantially planar membrane designed for use in a pressure-responsive IOP control system 200. The membrane 340 may have a thickness ranging from 1 to 15 μm. Membrane thickness, material, and diameter, in combination with the number, placement, and depth of the corrugations, all affect the cracking pressure of the corrugated membrane 340.

FIG. 7 depicts a cross-sectional side view taken along line 7-7 in FIG. 4, showing the corrugations within the corrugated membrane 340. Corrugated membranes may have a larger linear range than flat, uncorrugated membranes because of the reduction of radial stress in the membrane. The reduced influence of thermal stress and packaging stress, and the larger linear range of corrugated membranes may make corrugated membrane actuators more suitable for certain IOP control systems than flat, uncorrugated membrane actuators.

The characteristics and placement of the corrugations 450, 460 can affect both the amount and type of deflection of the membrane 340 at a given pressure differential across the membrane. Such variables or parameters may be customized in a given corrugated membrane to supply a given deflection profile as a function of the pressure differentials across the membrane. The use of a shallow corrugation zone 430 and a deep corrugation zone 410, for example, will affect the deflection profile, providing a nonlinear response to the applied pressure. As a result of the nonlinear response, the membrane may be designed to deflect greatly with minimal load by the use of deep corrugations, or deflect slightly with minimal load by the use of shallow corrugations. In other embodiments, the membrane may be designed to provide an opposite deflection profile, i.e., to deflect slightly with minimal load by the use of deep corrugations, or deflect greatly with minimal load by the use of shallow corrugations. The mechanical sensitivity and responsiveness of the membrane 340 may be controlled by selecting a particular combination of corrugation characteristics or parameters, which are often easier to control than the parameters of a membrane deposition or fabrication process.

In addition, in some embodiments, the greater the amplitude and/or the depth of the corrugations within a zone, and the closer the corrugations are to each other, the greater the flexibility of the membrane 340 that can be achieved in that particular zone. If the peak-to-peak dimensions or wavelengths of the corrugations 450, 460 are compared to the peak-to-valley depths or amplitudes of the corrugations 450, 460, a flexibility ratio can be established for each corrugation zone by dividing the depth by the corresponding wavelength. In some embodiments, the larger the flexibility ratio, the greater the response and deflection of that zone of the membrane 340 in response to a given pressure.

Also, the distance of the deep corrugation zone 410 and the shallow corrugation zone 430 from the membrane anchor points (i.e., the peripheral zone 400) will play a role in the behavior of the deflection profile of the membrane 340. Varying and mixing corrugation number, depth, and placement may enhance the controllability of the parameters that define membrane deflection at given pressure differentials. Specifically, the ability to control the deflection profile increases the degree of controllability of flow across the membrane valve 300 and allows for further fine tuning of flow properties and flow resistance. Thus, varying the number, position, depth, and arrangement of the corrugations 430 in the corrugated membrane 340 can affect the cracking pressure and operative fluid control of the valve 300.

FIG. 8 presents a diagrammatic representation of an exemplary mean membrane deflection curve 570 above the membrane 340. When the corrugated membrane 340 is operative in a valve 300, any pressure differential to which the membrane 340 is exposed will cause the membrane 340 to deflect or displace in one direction or the other, with the greatest axial displacement occurring at the central zone 440. As shown in FIG. 8, deflection of the membrane 340 is generally radially symmetric about the central zone 440. The mean deflection profile of the deep corrugation zone 410 is reflected by regions 580a, 580b of the mean deflection profile curve 570, and the mean deflection profile of the shallow corrugation zone 430 is reflected by regions 590a, 590b of the mean deflection profile curve 570. Comparison of the regions 580a, 580b and 590a, 590b indicates a steeper displacement slope for the deep corrugation zone 410 than the shallow corrugation zone 430. At certain pressure differentials, this relationship may be reversed. In other embodiments having different arrangements of deep and shallow corrugations, the mean membrane deflection curve may comprise any of a variety of different shapes and slopes, including by way of non-limiting example, asymmetrical shapes.

The use of membrane corrugations adds additional degrees of freedom to the valve design by allowing for an engineered nonlinear response to pressure differentials to drive the membrane valve to a specific open or closed or throttled position. The engineered nonlinear response corresponds to membrane deflection profiles that directly affect the resistance to flow across the valve, and provides a unique nonlinear flow profile that enables the membrane valve to have specific and reproducible response characteristics at various pressure differentials. For example, depending upon the specific characteristics of the corrugated membrane, the valve may have a quick or slow response, or a large or small deflection, to various pressure differentials.

Figure 9A:
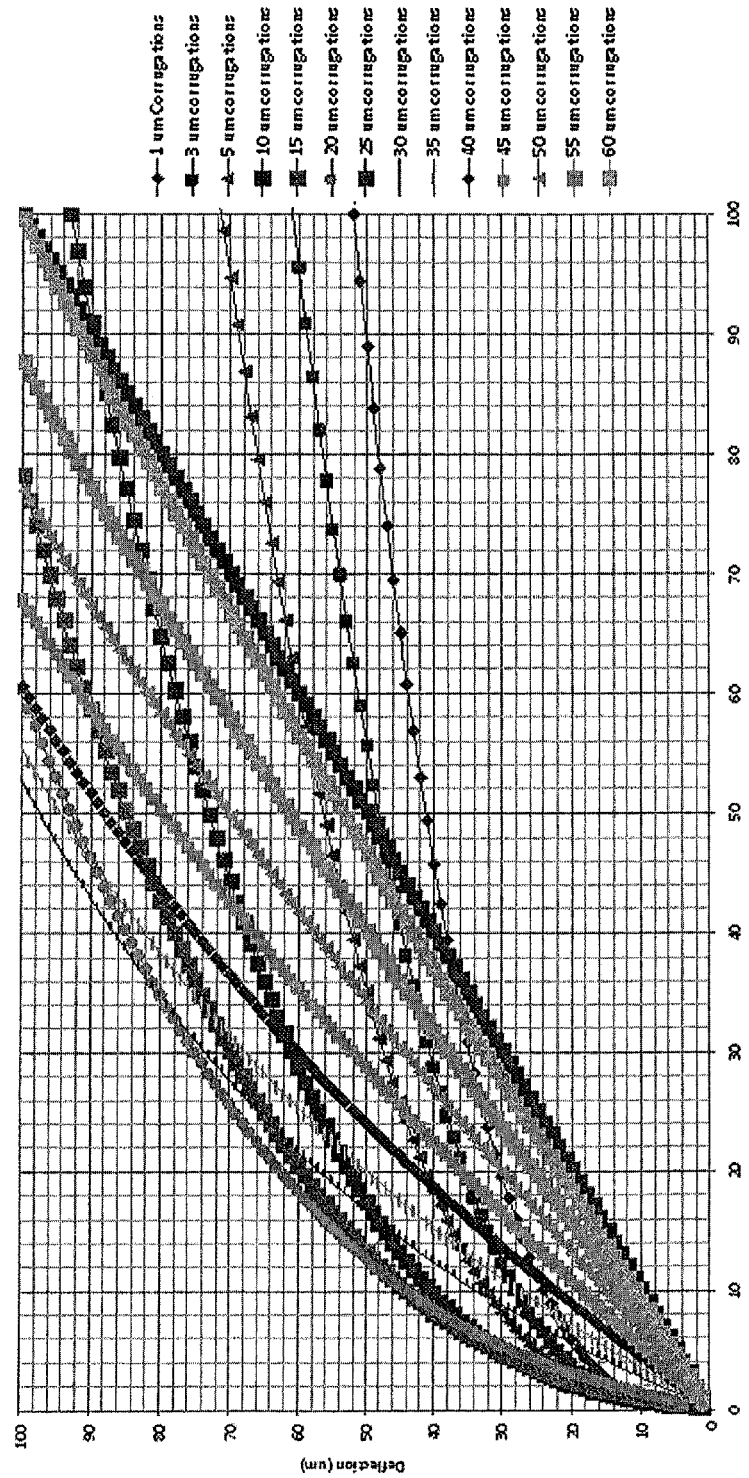
FIGS. 9a and 9b are graphical representations of membrane deflection to various pressure differentials for a series of different corrugation depths.
Figure 9B:
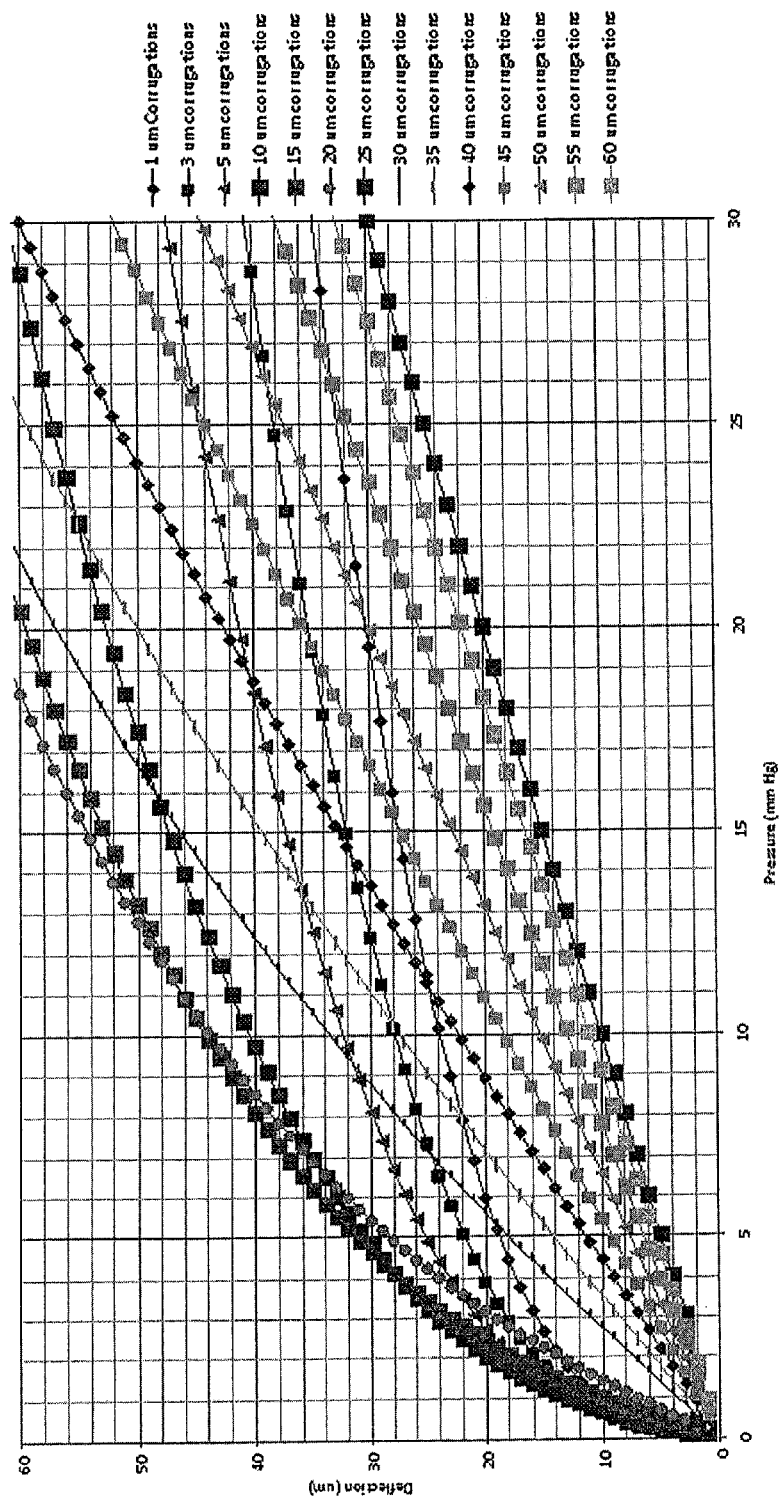

FIGS. 9a and 9b, for example, graphically illustrate how membranes having different corrugations depths may respond and deflect differently across a multitude of different pressure differentials. In FIGS. 9a and 9b, the x-axes correspond to pressure differentials acting on the membrane, and the y-axes correspond to the deflection of the membrane in response to the various pressure differentials.

Returning to FIG. 3, the valve 300 in shown in a closed, flow-blocking position. The valve 300 is in a closed position because the IOP (P1–P3) is not in excess of the cracking pressure of the valve 300, and the pressure of the reference chamber 320 forces the membrane 340 against the boss member 350. The surface 340b of the corrugated membrane 340 is resting on the sealing surface of the boss member 350, thereby blocking the flow of aqueous humor from the fluid inlet 380 to the fluid outlet 390 and through the drainage tube 210. It is desirable not to allow the IOP to drop below a certain threshold, for example, 6 mmHg. Any intraocular pressure below such a threshold is considered hypotonous pressure and is dangerous to the eye, as explained above. The valve system 220 is self-limiting because the pressure-driven valve 300 will not open unless the pressure differential across the valve 300 overcomes the cracking pressure of the valve. Accordingly, if the IOP (P1–P3) is lower than the cracking pressure of the corrugated membrane 340, then the valve 300 will not open and aqueous humor will not leave the anterior chamber 240 through the IOP control system 200.

FIG. 10 illustrates the valve 300 in an open, flow-permitting condition. Note that in the pictured embodiment in FIG. 3, the membrane 340 is stretched over the boss member 350 in a deformed state even when the valve 300 is at rest. When the IOP (P1–P3) is in excess of the cracking pressure of the valve 300 (equivalent to the target IOP), as shown in FIG. 10, the membrane 340 deforms further to rise off the boss member 350 and the valve 300 opens, thereby allowing aqueous humor to flow through the drainage tube 210 from the fluid inlet 380 to the fluid outlet 390 in the direction of the remaining valves and the drainage site 250. Accordingly, the valve 300 is in an open condition because the IOP (P1–P3) is in excess of the cracking pressure of the corrugated membrane 340 (equivalent to the target IOP), for example 12 mm Hg+/−1 mm Hg. The corrugated membrane 340 allows flow through the tube 210 by deflecting off the boss member 350 and into the reference chamber 320 in response to the pressure differential between the anterior chamber pressure (as reflected by pressure area P1 in the fluid inlet 380) against one side 340b of the corrugated membrane 340 and the dry subconjunctival pressure (as reflected by pressure area P3 in the reference chamber 320) against the opposite side 340a of the corrugated membrane 340. Because the valve 300 is in an open condition, the aqueous humor can flow through the drainage tube 210 from the fluid inlet 380 to the fluid outlet 390 in the direction of remaining valves and the drainage site 250. This ensures that drainage of the aqueous humor can occur through the drainage tube 210 if the IOP is elevated.

To ensure biocompatibility, the valve 300 may be coated or encapsulated in a biocompatible material including, but not be way of limitation, polypropylene, silicone, Parylene, or other known biocompatible materials.

Though the pressure-driven valve 300 is depicted as comprising a disk-like corrugated membrane and a boss member in FIG. 3, the valve 300 may be comprised of any of a number of different flow control elements that meter, restrict, or permit the flow of aqueous humor from the anterior chamber 240 to the drainage site 250. For example, trapped gaseous medium can be used in conjunction with a compliant membrane to enable the pressure-driven valves. In addition, the valve 300 may be positioned anywhere in fluid communication with the drainage tube 210, whether within or along the drainage tube 210.

Conventional passive check valves in drainage device implants (e.g., the Ahmed Valve) provide a reduced risk of hypotony in the weeks immediately following surgery. But these conventional valves have no mechanism for accounting for drainage site or bleb pressure. The systems disclosed herein may adjust to control flow to the bleb. Accordingly, the systems and methods disclosed herein provide a device that a) requires zero to minimal power (internal or external), and b) presents a mechanism of minimizing bleb height (reducing or eliminating bleb) by controlling the flow through the IOP control system 200 based controlling the deflection of membrane actuators in response to pressure differentials, which could significantly reduce the effect of fibrosis and also reduce or eliminate other issues related to bleb management.

The systems and methods described herein achieve IOP control with a very small pressure-sensitive device that utilizes corrugated membrane actuators and zero to very low power. The application of corrugated membrane actuators offers the possibility to control the sensitivity of the membranes by manipulating geometrical parameters (i.e., the depth, pattern, and number of corrugations), thus reducing the effect of variations in the initial membrane stress (e.g., due to variations in the membrane deposition process and/or the influence of temperature changes and packaging stresses).

The use of membrane corrugations allows for an engineered nonlinear response to pressure differentials to drive the membrane valve to a specific open or closed or throttled position. The engineered nonlinear response corresponds to unique membrane deflection profiles that directly affect flow through the membrane valve and enables the valve to have specific and fairly reproducible response characteristics to given pressure differentials. In addition, the system takes into account drainage or bleb pressure in regulating drainage flow. Accordingly, the system provides suitable care for a patient suffering from irregular intraocular pressure by utilizing corrugated membrane valves to control the flow rate of aqueous humor through the drainage device.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. An intraocular pressure (IOP) control valve for implantation in an eye of a patient, comprising:
    a housing including a fluid inlet and a fluid outlet; and
    a corrugated membrane anchored within the housing to form a reference chamber on a first side of the corrugated membrane and a fluid flow channel on a second opposing side of the membrane, the reference chamber having a reference chamber pressure representative of atmospheric pressure, the fluid flow channel selectively increasing and decreasing in size to permit fluid to flow from the fluid inlet to the fluid outlet, the corrugated membrane configured to affect flow through the fluid flow channel from the fluid inlet to the fluid outlet by deflecting in response to pressure differentials of the reference chamber pressure and the fluid flow channel pressure acting on the opposing sides of the corrugated membrane.

2. The IOP control valve of claim 1, the housing further including a first housing section and a second housing section, wherein the corrugated membrane is anchored between the first housing section and the second housing section.

3. The IOP control valve of claim 1, wherein the fluid flow channel comprises a gap between the fluid inlet and the corrugated membrane.

4. The IOP control valve of claim 1, wherein the corrugated membrane is configured to control flow through the fluid flow channel by deflecting in response to pressure differentials between an anterior chamber of the eye and atmospheric pressure acting on the corrugated membrane.

5. The IOP control valve of claim 1, wherein the corrugated membrane comprises a flexible, fluid-tight membrane configured to deflect away from the fluid inlet in response to an elevated IOP.

6. The IOP control valve of claim 1, further comprising a boss member positioned within the housing between the fluid inlet and the fluid outlet.

7. The IOP control valve of claim 6, wherein the boss member comprises a toroid, raised member circumferentially surrounding the fluid inlet.

8. The IOP control valve of claim 6, wherein the corrugated membrane comprises a flexible, fluid-tight membrane configured to deflect away from the boss member in response to an elevated IOP.

9. The IOP control valve of claim 1, wherein the corrugated membrane comprises a circular membrane including a plurality of annular, concentric corrugations.

10. The IOP control valve of claim 9, wherein the plurality of corrugations are arranged in a plurality of corrugated zones possessing corrugations of varying amplitudes and depths.

11. The IOP control valve of claim 10, wherein the corrugated membrane comprises an uncorrugated central zone configured to seal the fluid inlet when the membrane is deflected toward the fluid inlet, and wherein the plurality of corrugated zones are positioned at varying radial distances from the uncorrugated central zone.

12. The IOP control valve of claim 11, wherein the central zone comprises a raised portion of the membrane configured to seal the fluid inlet when the membrane is deflected toward the fluid inlet.

13. The IOP control valve of claim 11, wherein the plurality of corrugations comprises a first corrugated zone including corrugations of a first depth and a second corrugated zone including corrugations of a second depth, wherein the first corrugated zone is positioned a first distance from the central zone of the membrane, and the second corrugated zone is positioned a second distance from the central zone of the membrane.

14. The IOP control valve of claim 13, wherein the first depth is greater than the second depth.

15. The IOP control valve of claim 13, wherein the first depth is substantially identical to the second depth.

16. An intraocular pressure (IOP) control system for implantation in an eye of a patient, comprising:
    a drainage tube configured to convey aqueous humor from an anterior chamber of the eye; and
    a pressure-driven membrane valve in fluid communication with the drainage tube and including a membrane having peaks and valleys formed therein, the valve being actuatable in response to pressure differentials and the membrane being configured to control flow rates of the aqueous humor along the drainage tube by deflecting in response to pressure differentials acting on the membrane.

17. The IOP control system of claim 16, wherein the membrane comprises a circular membrane and wherein the peaks and valleys form a plurality of annular, concentric corrugations, and each corrugation includes a first sidewall connecting a peak to a neighboring valley and a second sidewall connecting the neighboring valley to a second peak.

18. The IOP control system of claim 17, wherein the first sidewall of at least one of the plurality of corrugations varies in amplitude or depth from a sidewall of at least one other of the plurality of corrugations.

19. The IOP control valve of claim 17, wherein the plurality of corrugations are arranged in a plurality of corrugated zones possessing corrugations of varying amplitudes and depths, and wherein the plurality of corrugated zones are positioned at varying radial distances from a center of the membrane.

20. The IOP control valve of claim 19, wherein the membrane includes a first corrugated zone including corrugations of a first depth and a second corrugated zone including corrugations of a second depth, wherein the first corrugated zone is positioned a first distance from the center of the membrane, and the second corrugated zone is positioned a second distance from the center of the membrane.

21. The IOP control valve of claim 20, wherein the first depth is greater than the second depth.

22. The IOP control valve of claim 20, wherein the first depth is substantially identical to the second depth.

23. The IOP control system of claim 17, the pressure-driven membrane valve further comprising a housing including a fluid inlet and a fluid outlet, wherein the membrane is anchored within the housing to form a reference chamber on a first side of the membrane and a fluid flow channel on a second side of the membrane, the fluid flow channel selectively increasing and decreasing in size to permit fluid to flow from the fluid inlet to the fluid outlet, the membrane configured to affect flow through the fluid flow channel from the fluid inlet to the fluid outlet by deflecting in response to pressure differentials acting on the sides of the membrane.

24. The IOP control system of claim 23, wherein the membrane is configured to control flow through the fluid flow channel by deflecting in response to pressure differentials between an anterior chamber of the eye and atmospheric pressure acting on the membrane.

25. The IOP control system of claim 23, the housing further including a first housing section and a second housing section, wherein the membrane is anchored between the first housing section and the second housing section.

26. The IOP control system of claim 23, wherein the fluid flow channel comprises a gap between the fluid inlet and the membrane.

27. The IOP control system of claim 23, wherein the membrane comprises a flexible, fluid-tight membrane configured to deflect away from the fluid inlet in response to an elevated IOP in the anterior chamber of the eye.

28. The IOP control system of claim 23, further including a boss member positioned within the housing between the fluid inlet and the fluid outlet, wherein the fluid flow channel comprises a gap between the boss member and the corrugated membrane.

29. The pressure-driven IOP control valve of claim 28, wherein the corrugated membrane closes the fluid flow channel by deflecting against the boss member to block the fluid inlet in response to pressure differentials acting on the sides of the membrane.

30. A method of regulating pressure through adjusting drainage from an anterior chamber of an eye with a membrane valve, comprising:
 directing fluid through a fluid flow channel formed in part by a flexible membrane shaped with at least one corrugation including a peak, a valley, and a sidewall extending at a first angle between the peak and the valley;
 modifying the amount of drainage through the membrane valve in response to pressure acting on the flexible membrane by deflecting the membrane to change the first angle to a second, different angle relative to the peak and valley, and to increase or decrease the size of the fluid flow channel in the membrane valve.

31. The method of claim 30, wherein the flexible membrane comprises a circular membrane including a plurality of annular, concentric corrugations.

32. The method of claim 31, wherein the plurality of corrugations are arranged in a plurality of corrugated zones possessing sidewalls of varying amplitudes and depths.

33. The method of claim 32, wherein the membrane comprises an uncorrugated central zone, and wherein the plurality of corrugated zones are positioned at varying radial distances from the uncorrugated central zone.

34. The method of claim 30, wherein modifying the amount of drainage through the membrane valve in response to pressure comprises deflecting the membrane to increase the size of the fluid flow channel in response to an elevated intraocular pressure (IOP).

35. The method of claim 30, wherein modifying the amount of drainage through the membrane valve in response to pressure comprises deflecting the membrane in response to pressure differentials between the anterior chamber of the eye and atmospheric pressure acting on the membrane.

* * * * *